US00PP28933P2

(12) United States Plant Patent
Caster et al.

(10) Patent No.: US PP28,933 P2
(45) Date of Patent: Feb. 6, 2018

(54) BLUEBERRY PLANT VARIETY NAMED 'DRISBLUEFIFTEEN'

(50) Latin Name: ***Vaccinium corymbosum* L.**
Varietal Denomination: DrisBlueFifteen

(71) Applicant: Driscoll's, Inc., Watsonville, CA (US)

(72) Inventors: Brian K. Caster, Salinas, CA (US); Arlen Draper, Payson, AZ (US); Jennifer K. Izzo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 6 days.

(21) Appl. No.: 14/999,884

(22) Filed: Jul. 13, 2016

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./156, 157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| 2016/0227685 | P1 | 8/2016 | Caster et al. |

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of blueberry plant named 'DrisBlueFifteen' particularly distinguished by producing later fruit having skin without bloom on immature fruit that is greyed-purple in color, skin without bloom on mature fruit that is dark blue in color, and skin with bloom on mature fruit that is light violet-blue in color, post-harvest fruit that can be stored for two weeks without a significant deterioration in quality, and having a plant with an average height of 138.4 cm, an average width of 185.5 cm, and a semi-erect growth habit, is disclosed.

3 Drawing Sheets

Latin name: Botanical classification: *Vaccinium corymbosum* L.

Varietal denomination: The varietal denomination of the claimed variety of blueberry plant is 'DrisBlueFifteen'.

BACKGROUND OF THE INVENTION

Blueberry plants are perennial flowering plants with indigo-colored berries from the section Cyanococcus within the genus *Vaccinium*. Many commercially sold species with English common names, including blueberry, are currently classified in section Cyanococcus of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L), which has been denominated as 'DrisBlueFifteen'.

Blueberry plant variety 'DrisBlueFifteen' was discovered in Santa Cruz County, Calif. in September of Year 1 and originated from a cross between the proprietary female parent blueberry plant 'MS122' and the proprietary male blueberry plant 'MS6'. The original seedling of the new variety was selected for its superior fruit quality, size, and appearance, as well as its production of a large healthy plant. The original seedling of the new variety was first asexually propagated via softwood cuttings at a nursery in Monterey County, Calif. in Year 1. 'DrisBlueFifteen' was subsequently asexually propagated via softwood cuttings and underwent further testing at a ranch in Santa Cruz County, Calif. for ten years (Year 3 to Year 12). The present invention has been found to be stable and reproduce true to type through successive asexual propagations via softwood cuttings.

'DrisBlueFifteen' exhibits the following distinguishing characteristics grown under normal horticultural practices in Santa Cruz County, Calif.:

1. Later fruit having skin without bloom on immature fruit that is greyed-purple in color, skin without bloom on mature fruit that is dark blue in color, and skin with bloom on mature fruit that is light violet-blue in color;
2. Post-harvest fruit that can be stored for two weeks without a significant deterioration in quality; and
3. Plant has an average height of 138.4 cm, an average width of 185.5 cm, and a semi-erect growth habit.

BRIEF DESCRIPTION OF THE DRAWINGS

This new blueberry plant is illustrated by the accompanying photographs which show fruit of the plant, as well as the flowers and leaves. The colors shown are as true as can be reasonably obtained by conventional photographic procedures. The photographs are of plants that are 13 years old.

DETAILED BOTANICAL DESCRIPTION

The following description sets forth the distinctive characteristics of 'DrisBlueFifteen'. The data which define these characteristics is based on observations taken in Santa Cruz County, Calif. from Year 3 to Year 12. This description is in accordance with UPOV terminology. Color designations, color descriptions, and other phenotypical descriptions may deviate from the stated values and descriptions depending upon variation in environmental, seasonal, climatic and cultural conditions. 'DrisBlueFifteen' has not been observed under all possible environmental conditions. The botanical description of 'DrisBlueFifteen' was taken from 13 year-old plants. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

Classification:

*Family*.—Ericaceae.

*Botanical*.—*Vaccinium corymbosum* L.

*Common name*.—Blueberry.

*Variety name*.—'DrisBlueFifteen'.

Parentage:

*Female parent*.—The proprietary blueberry plant 'MS122'.

*Male parent*.—The proprietary blueberry plant 'MS6'.

Plant:

*Size*.—Medium.

*Height*.—138.4 cm.

*Width*.—185.5 cm.

*Length/width ratio*.—0.7.

*Plant vigor*.—Strong.

*Growth habit*.—Semi-erect.

*Productivity*.—Up to 5 pounds of fruit per plant.

*Cold hardiness*.—Medium; USDA Plant Hardiness Zone 6.

*Chilling requirement*.—Up to 300 hours.

*Propagation*.—Soft wood cuttings.

*Time of vegetative bud burst*.—March to April.

*Fruiting type*.—Only on one-year-old shoots.

*Cane renewal*.—Strong.

*Internode length* (*upper half on one-year old shoot*).—15.9 mm.

*One-year old canes* (*young canes*).—Length: 48.7 cm. Diameter at the base: 6.0 mm. Diameter at the tip: 1.7 mm. Texture: Smooth. Color (One-year old shoot, branch and canes): RHS 144C (Light yellow-green).

*Five-year old canes* (*mature canes*).—Length: 108.2 cm. Diameter at the base: 21.1 mm. Diameter at the tip: 1.8 mm. Texture: Rough. Color: RHS 201B (Medium grey).

Figure 1:
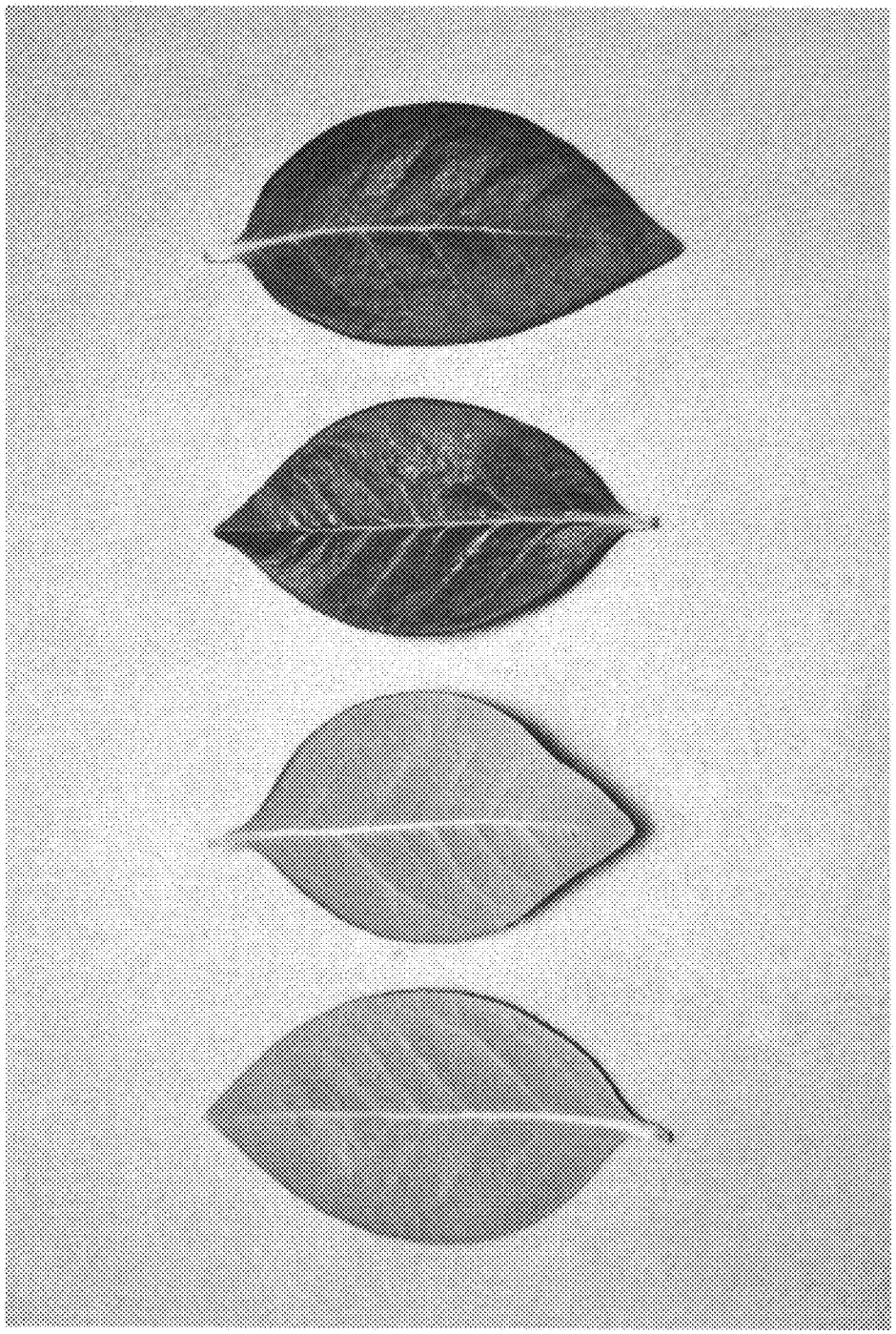
FIG. 1 illustrates leaves of variety 'DrisBlueFifteen'.

Mature leaves (FIG. 1):

*Length*.—Medium; 51.9 mm.

*Width*.—Medium; 29.9 mm.

*Length/width ratio*.—1.7; Longer than broad.

*Period of appearance of leaf bud*.—Early.

*Shape*.—Elliptic.

*Apex*.—Cuspidate.

*Base*.—Cuneate.

*Margin*.—Entire.

*Pubescence*.—Glabrous (Absent).

*Sheath*.—Absent.

*Arrangement*.—Alternate.

*Venation*.—Reticulate.

*Color*.—Upper surface: Dark; RHS N137 (Dark green). Lower surface: Light; RHS 194AC (Light greyed-green).

*Internode length of shoots*.—Medium; 15.90 mm.

Petiole:

*Length*.—3.2 mm.

*Diameter*.—1.51 mm.

*Color*.—RHS 142C (Light green).

Figure 2:
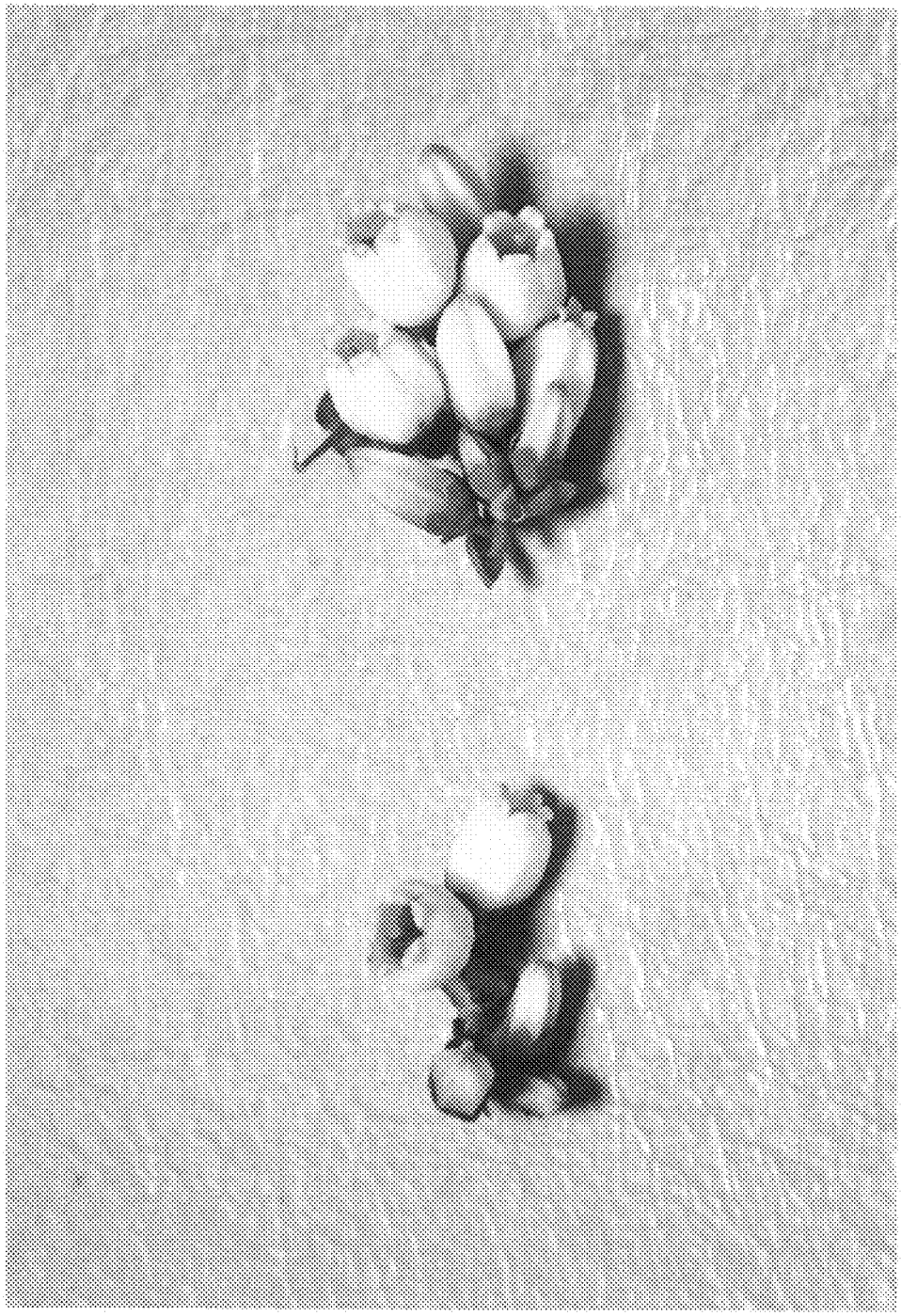
FIG. 2 illustrates flowers of variety 'DrisBlueFifteen'.

Flowers (FIG. 2):

*Length* (*excluding peduncle*).—Medium; 8.23 mm.

*Diameter*.—6.52 mm.

*Length/width ratio*.—1.3.

*Color*.—RHS 155B (White).

*Flower bud*.—Length: 5.2 mm. Width: 3.7 mm. Number of flowers per bud or peduncle: 6. Anthocyanin coloration: Very weak; RHS 64B (Medium red-purple). Color on immature buds: Dark; RHS 183A (Dark greyed-purple). Color on mature buds: Medium; RHS 64B (Medium red--purple).

*Petal width* (*ridge to ridge*).—4.22 mm.

*Fragrance*.—Between faint and medium.

*Time of beginning flowering on one-year shoot*.—Between early and medium.

*Pedicel*.—Length: 5.5 mm. Diameter: 1.1 mm. Color: RHS 142C (Light green).

*Corolla*.—Aperture diameter: 2.74 mm. Shape: Urceolate (Urn-shaped). Size of corolla tube: Medium. Anthocyanin coloration of corolla tube: Very weak RHS 64B (Medium red-purple). Ridges on tube: Present.

*Peduncle*.—Length: 13.9 mm. Surface texture: Smooth. Color: RHS 144C (Medium yellow-green).

Reproductive organs:

*Style length* (*including stigma*).—7.91 mm.

*Ovary color*.—RHS 191B (Medium greyed-green).

*Pollen amount*.—Medium.

*Pollen color*.—RHS 4D (Light yellow).

*Anther color*.—RHS 167A (Medium greyed-orange).

Figure 3:
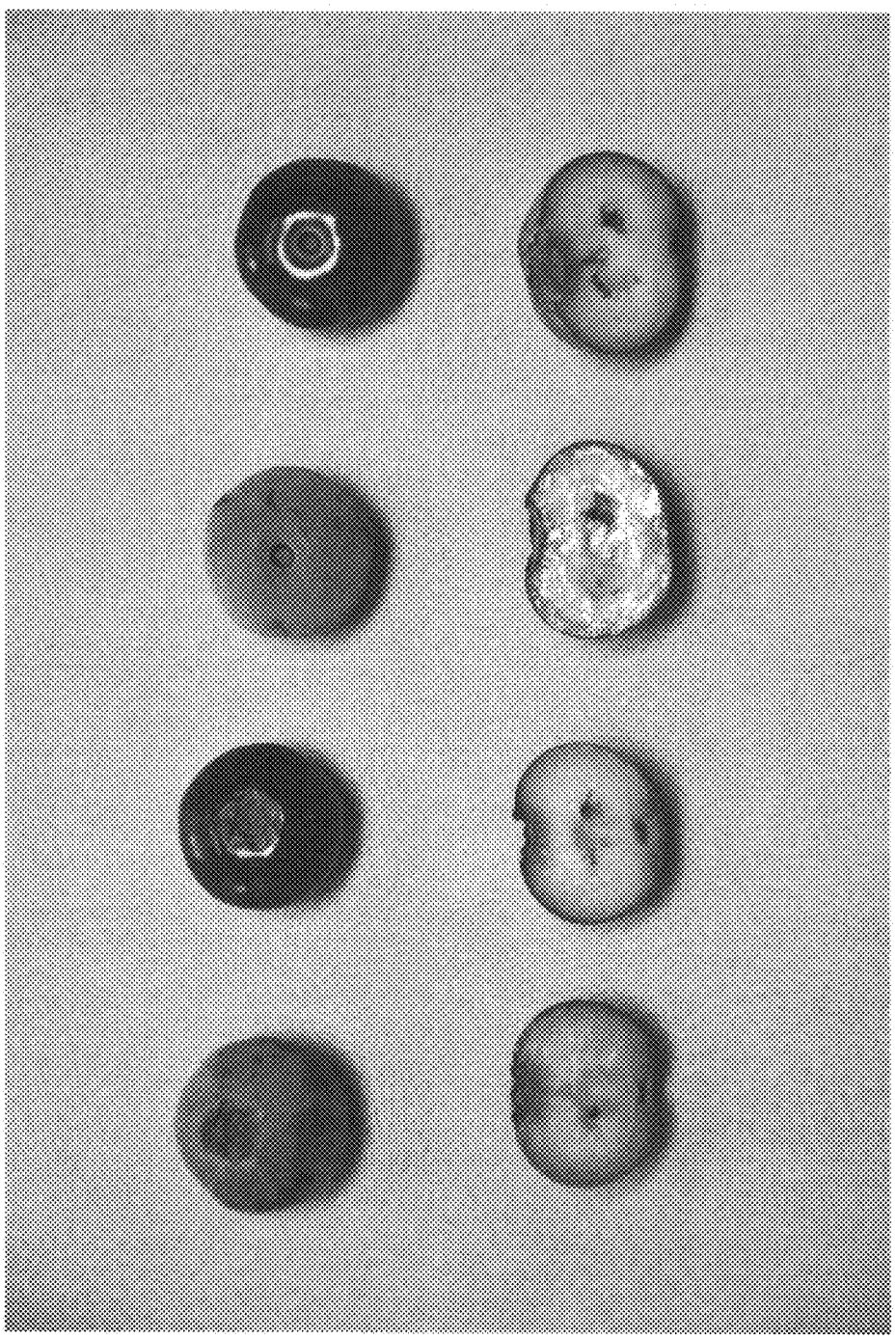
FIG. 3 illustrates whole fruit and a cross-section of the fruit of variety 'DrisBlueFifteen'.

Fruit (FIG. 3):

*Size*.—Medium.

*Length*.—13.53 mm.

*Diameter*.—17.82 mm.

*Length/width ratio*.—0.8.

*Fruit pedicel diameter*.—1.1 mm.

*Weight*.—3.6 g.

*Number of berries per cluster*.—6.

*Cluster density*.—Sparse or low.

*Shape in longitudinal sections*.—Oblate.

*Intensity of green color* (*immature fruit with bloom*).—Light or clear; RHS 138C (Light green).

*Color of skin without bloom on immature fruit*.—RHS 183A (Greyed-purple).

*Color of skin without bloom on mature fruit*.—RHS 103A (Dark blue).

*Color of skin with bloom on mature fruit*.—RHS 98D (Light violet-blue).

*Intensity of bloom on mature fruit*.—Strong.

*Attitude of sepals*.—Incurving.

*Calyx*.—Diameter of basin: Medium; 4.31 mm. Depth of basin: Medium; 2.24 mm. Diameter/depth ratio: 1.9.

*Flesh color*.—RHS 145C (Light yellow-green).

*Firmness*.—Very firm.

*Sweetness*.—11 Brix.

*Time of beginning of fruit ripening on one-year old shoots*.—May.

*Harvest season*.—May to August.

*Harvest interval*.—Late May to early August.

*Shipping and storage characteristics*.—Fruit can be stored for two weeks without significant deterioration.

Seeds:

*Length*.—1.61 mm.

*Width*.—0.89 mm.

*Length/width ratio*.—1.8.

*Abundance*.—Medium.

*Color*.—RHS 172B (Medium greyed-orange).

Resistance to pests and diseases: No known resistances.

COMPARISONS TO COMMERCIAL BLUEBERRY VARIETIES

'DrisBlueFifteen' differs from commercial blueberry plant variety 'DrisBlueSeven' (U.S. Plant Pat. No. 24,605) in that 'DrisBlueFifteen' produces fruit later than does 'DrisBlueSeven'. Moreover, the the skin color without bloom of immature fruit of 'DrisBlueFifteen' is RHS 183A (greyed-purple), while the skin color without bloom of immature fruit of 'DrisBlueSeven' is RHS 59A (dark red-purple). Further, plants of 'DrisBlueFifteen' are medium in size, whereas plants of 'DrisBlueSeven' are large to very large. Flowers of 'DrisBlueFifteen' have a faint-medium fragrance, whereas flowers of 'DrisBlueSeven' have a very faint or absent fragrance. Additionally, 'DrisBlueFifteen' has a harvest interval that ranges front late May to early August, whereas 'DrisBlueSeven' has a harvest interval that ranges from mid-May to mid-September.

'DrisBlueFifteen' differs from commercial blueberry plant variety 'DrisBlueFive' (U.S. Plant Pat. No. 24,489) in that plants of 'DrisBlueFifteen' are taller and wider while being less bushy than plants of 'DrisBlueFive'. 'DrisBlueFifteen' also produces immature fruit with a skin color without bloom of RHS 183A (greyed-purple) and mature fruit with a skin color without bloom of RHS 103A (dark blue), while 'DrisBlueFive' produces immature fruit with a skin color without bloom of RHS N77A (dark purple) and mature fruit with a skin color without bloom of RHS N186A (light blue). Further, the fruit of 'DrisBlueFifteen' has a high sweetness, whereas the fruit of 'DrisBlueFive' has a medium sweetness. Flowers of 'DrisBlueFifteen' have a faint-medium fragrance, whereas flowers of 'DrisBlueFive' have a very faint or absent fragrance. Additionally, 'DrisBlueFifteen' has a harvest interval that ranges from late May to early August, whereas 'DrisBlueFive' has a harvest interval that ranges from early May to early July.

What is claimed is:

1. A new and distinct variety of blueberry plant designated 'DrisBlueFifteen' as shown and described herein.

* * * * *